United States Patent [19]

Morrissey et al.

[11] Patent Number: 5,531,231
[45] Date of Patent: *Jul. 2, 1996

[54] APPARATUS AND METHOD FOR CONTROLLING HUMAN LACTATION

[76] Inventors: Gerald Morrissey; Suzanne Morrissey, both of 3 Lake View Cir., Skaneateles, N.Y. 13152

[*] Notice: The term of this patent shall not extend beyond the expiration date of Pat. No. 5,394,889.

[21] Appl. No.: 396,921

[22] Filed: Mar. 1, 1995

Related U.S. Application Data

[63] Continuation-in-part of Ser. No. 954,012, Sep. 30, 1992, Pat. No. 5,394,889.

[51] Int. Cl.⁶ ............................ A61F 5/37; A61J 13/00
[52] U.S. Cl. ............................................. 128/846; 128/890
[58] Field of Search .................................... 128/846, 890; 604/366, 370, 377, 378, 381, 383; 450/36–41, 45, 57, 63, 68; 623/7

[56] References Cited

U.S. PATENT DOCUMENTS

| | | |
|---|---|---|
| 1,671,342 | 5/1928 | Cantor. |
| 2,834,352 | 5/1958 | Ullian. |
| 2,891,544 | 6/1959 | London. |
| 4,164,228 | 8/1979 | Weber-Unger ........................... 128/890 |
| 4,333,471 | 6/1982 | Nakai ...................................... 128/890 |
| 4,566,458 | 1/1986 | Weinberg. |
| 4,681,587 | 7/1987 | Eberl ............................................ 623/7 |
| 4,778,465 | 10/1988 | Wilkins ....................................... 623/7 |
| 4,870,977 | 10/1989 | Imonti ......................................... 623/7 |
| 4,875,492 | 10/1989 | Mitchell ................................. 128/890 |
| 5,032,103 | 7/1991 | Larsson. |

FOREIGN PATENT DOCUMENTS

| | | |
|---|---|---|
| 1133702 | 4/1957 | France. |
| 377643 | 6/1921 | Germany. |
| 177295 | 3/1922 | United Kingdom. |

OTHER PUBLICATIONS

P. 78 in *The Womanly Art of Breast Feeding*, J. Torgas, ed., La Leche League International, New York, N.Y. (1987).

*Primary Examiner*—Michael A. Brown
*Attorney, Agent, or Firm*—Nixon, Hargrave, Devans & Doyle

[57] ABSTRACT

An apparatus comprising a support having an outer surface and an inner surface that is shaped to conform substantially to a human female breast and having a protrusion with a substantially flat, nipple-contacting surface which extends away from the support and is positioned to align substantially with and contact a nipple of a human female breast prevents a human female breast from lactating when placed over the breast. The present invention also provides a method for controlling human lactation which utilizes the present apparatus and includes the steps of placing and positioning the apparatus over the breast and applying pressure on the apparatus sufficient to prevent lactation.

19 Claims, 2 Drawing Sheets

APPARATUS AND METHOD FOR CONTROLLING HUMAN LACTATION

FIELD OF INVENTION

This application is a continuation-in-part of application Ser. No. 07/954,012, filed on Sep. 30, 1992, now U.S. Pat. No. 5,384,889. The present invention relates to an apparatus and method for controlling lactation in human females.

BACKGROUND OF THE INVENTION

In recent years, breastfeeding of newborn babies has seen a resurgence in popularity. Breastfeeding is becoming more popular for a variety of reasons relative to both baby and mother. These advantages include increased protection of the infant from illness through the development of protective antibodies, decreased risk of developing childhood cancers, avoiding potential allergies to commercial infant formulas, and enhanced jaw, teeth, and speech development, among others. Furthermore, it has been suggested that nursing mothers have a lower risk of developing breast cancer. Breast feeding has also been suggested to improve the emotional bond between mother and child.

Although breast feeding is enjoying renewed use, it is not without disadvantages. The outpouring of milk is known as the "let-down" or "milk-ejection" reflex. A let-down can occur several times during a feeding. It is well known that the milk-ejection reflex can be triggered at inappropriate times by various stimuli. A baby's crying, for example, may cause let-down in a nursing mother. This can result in let-down at very inopportune times.

This inappropriate let-down can be particularly problematic for working mothers who are nursing. Solutions designed to alleviate problems associated with inappropriate let-down include absorbent breast pads or breast shields that operate, essentially, as a well or reservoir to collect leaking milk. These solutions are disadvantageous because of the limited capacity of both types of devices as well as the likelihood that milk will leak into clothing despite their use.

It is also known that nursing mothers can apply direct pressure to the nipples with the heels of their hands or forearms to temporarily halt leakage. However, this type of solution likewise presents obvious disadvantages for the nursing mother who is working or otherwise in public.

Controlling lactation in mothers with "inverted nipples" has been particularly problematic. An inverted nipple is a nipple that does not protrude or become erect and extend away from the areolar region. Since the nipple is sunk into the areolar region, accessing the nipple to apply pressure and control or stop leakage is more difficult than with non-inverted nipples.

In addition to controlling lactation, stopping lactation in women, who for personal or medical reasons have decided not to breastfeed and want to dry up has also been difficult. One option for stopping lactation has been the use of drug therapy, however the use of drug therapy has come under intense scrutiny because of the serious side effects these drugs have produced. The other existing option to stop lactation has been a binding process. Elastic bandages are tightly wrapped around a woman's body covering her breasts and nipples. The bandages can potentially stop lactation, but put severe pressure on the woman's back and mammary glands which is very uncomfortable and can have negative side effects (i.e., mastitis, plugged ducts, etc.). Therefore, there continues to be a need for apparatus that can effectively control and/or stop lactation in mothers, particularly those with at least one inverted nipple.

SUMMARY OF THE INVENTION

This invention relates to an apparatus and method for controlling human lactation. The apparatus comprises a support having an outer surface and an inner surface that is shaped to conform substantially to a human female breast. The inner surface has a protrusion with a substantially flat, nipple-contacting surface which extends away from the support and is positioned to align substantially with and contact a nipple of a human female breast when the apparatus is placed over the breast. In this way, the substantially flat, nipple contacting surface of the protrusion prevents the breast, even with an inverted or flat nipple, from lactating. The method includes the steps of placing the apparatus over the breast and applying pressure on the apparatus sufficient to prevent lactation.

The apparatus and method of the present invention provide a convenient and effective way to control and/or stop milk leakage in the nursing mother, even with mothers with inverted nipples. The apparatus can be inexpensively constructed in a variety of shapes from a variety of materials.

DETAILED DESCRIPTION OF THE INVENTION

Figures 1, 2, 3:
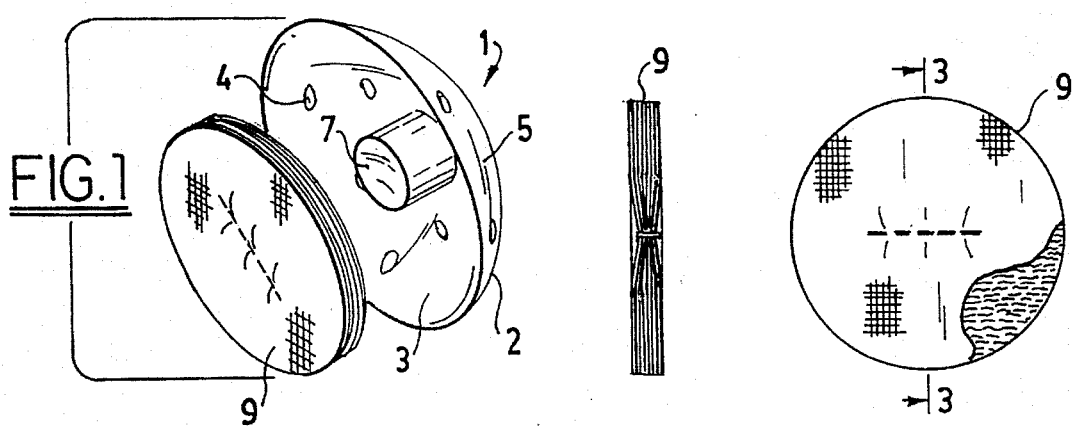
FIG. 1 is an exploded, perspective view of one embodiment of the apparatus of the present invention and an absorbent breast pad.
FIG. 2 is a front view of an absorbent breast pad.
FIG. 3 is a side view of an absorbent breast pad.
Figure 7:
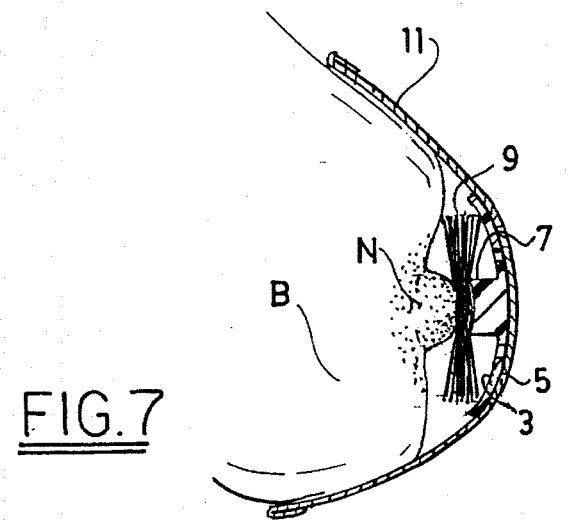
FIG. 7 is a cross-sectional side view of the apparatus, including a brassiere, placed over a human female breast.

FIG. 1 is an exploded, perspective view of one embodiment of the apparatus of the present invention and an absorbent breast pad. Apparatus 1 includes support 2 having an inner surface 3 and an outer surface 5. Inner surface 3 has a protrusion 7 which extends away from support 2. Referring to FIG. 7, which is a cross-sectional side view of one embodiment of the present apparatus, including a brassiere, placed over a human breast, protrusion 7 is positioned to align substantially with and contact nipple N of human female breast B. Protrusion 7 operates to depress nipple N, whereby breast B is prevented from lactating.

Support 2 is shaped to conform substantially to a human female breast. Support 2 can, for example, be substantially circular with a concave/convex shape covering a relatively small area of breast B as shown in FIG. 7. Support 2 can also take a variety of other forms, substantially conforming to larger or smaller areas of breast B. Preferably, support 2 is constructed in a substantially circular, concave/convex form and having a radius from about 3 to 5 inches for maximum comfort and to allow use of the apparatus on breasts of various sizes. Most preferably, support 2 is shaped such that suction is created between breast B and apparatus 1 after apparatus 1 is placed over breast B. The suction helps to maintain the alignment of apparatus 1 with nipple N.

Figures 4, 5, 6:
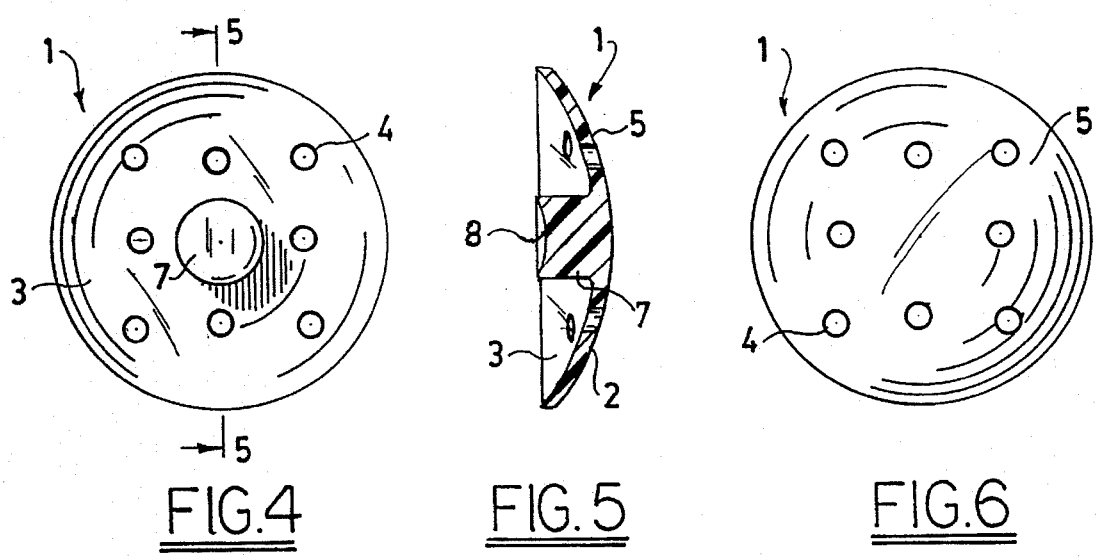
FIG. 4 is a perspective view of the inner surface and protrusion of the apparatus.
FIG. 5 is a cross-sectional side view of FIG. 4 taken along line 5—5.
FIG. 6 is a perspective view of the outer surface of the support of the apparatus.

Support 2 can be made from a variety of flexible materials including moldable plastic or rubber. Preferably, support 2 is made from a moldable, flexible plastic material to allow maximum comfort and ease of manufacture. With reference to FIGS. 4 and 6, perspective views of the inner and outer surfaces, respectively, of support 2, support 2 can be provided with holes 4 to allow air circulation around the nipple and areolar region of breast B to help prevent local irritation which commonly occurs in nursing mothers.

Protrusion 7 can be produced separately and then attached to inner surface 3 or, preferably, integrated with inner surface 3. This preferred embodiment is shown by FIG. 5, a cross-sectional side view of FIG. 4 taken along line 5—5. Protrusion 7 can be integrated with inner surface 3 by molding protrusion 7 and support 2 together from the same material. Protrusion 7 can be made from a variety of materials, as long as the material is sufficiently rigid to depress nipple N when nipple N is contacted by protrusion 7. Exemplary materials for forming protrusion 7 include any of the rigid plastics known in the art or sufficiently rigidized rubber.

Figure 8:
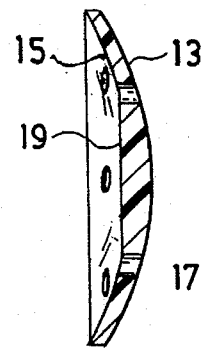
FIG. 8 is a cross-sectional side view of an alternative embodiment of the inner surface of the support and protrusion of the present invention.

Protrusion 7 can be any shape, so long as it is capable of depressing nipple N when apparatus 1 is brought into contact with breast B and, in turn, preventing lactation. For example, protrusion 7, can be a flattened, planar surface formed in the center of the inner surface 3 of support 2, as shown by FIG. 8, a cross-sectional side view of an alternative embodiment of the inner surface of the support and protrusion of the present invention. Protrusion 7 is preferably cylindrical, having a size approximating a human female nipple, as shown in FIG. 7. Most preferably, as illustrated by FIGS. 5 and 7, nipple-contacting surface 8 of protrusion 7 is concave to make the apparatus more comfortable for the wearer and aid in keeping apparatus 1 in place.

Preferably, absorbent pad 9 is placed over inner surface 3 to absorb any small amount of leakage resulting, for example, from misalignment of protrusion 7 and nipple N, as well as any other moisture surrounding the nipple and areolar region. This embodiment is illustrated by FIGS. 1 and 7.

As shown by FIG. 7, the above-described apparatus can be used by placing it over breast B and applying pressure to the apparatus sufficient to depress and, in turn, prevent milk release by nipple N of breast B. The amount of pressure need not be great and can normally be produced by the force provided when apparatus 1 further comprises brassiere 11. Support 2 can be placed inside the cup of brassiere 11 which is then put on by the lactating woman, as illustrated by FIG. 7. Support 2 can either be manually placed into or actually integrated with (e.g., sewn into) the cup of the brassiere. Brassiere 11 can be a conventional or nursing brassiere commonly worn by nursing mothers.

Figure 9:
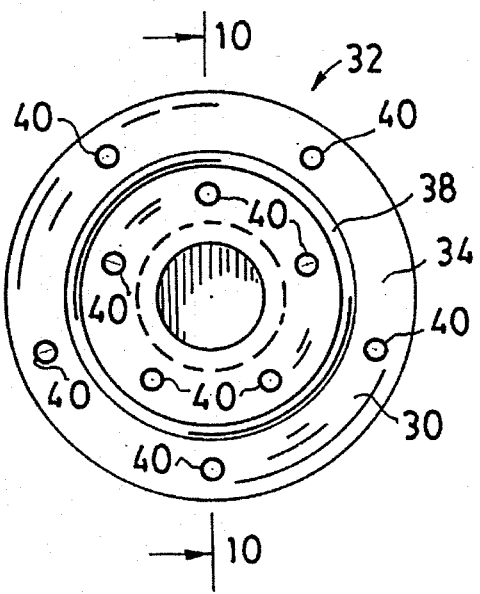
FIG. 9 is a perspective view of an outer surface for another embodiment of the apparatus.

Referring to FIG. 9, a perspective view of an outer surface 30 for apparatus 32 is illustrated. Apparatus 32 includes support 34 which is shaped to substantially conform to a human female breast and has outer surface 30, an inner surface 36 (shown in FIG. 10), a raised ring 38, and a plurality of air holes 40. In this particular embodiment, support 34 has a substantially circular shape, although support 34 could have other shapes, such as oval. Support 34 can be made from a variety of materials, including plastic and rubber.

Raised ring 38 extends out and away from outer surface 30 of support 34. When apparatus 32 is disposed in the cup of brassiere 11, raised ring 38 catches against the inside of the cup to help keep support 34 in place against the woman's breast B'. Although only one raised ring 38 is shown, support 34 can have as may raised rings 30 on outer surface 30 as desired.

Air holes 40 extend through support 34 between outer and inner surfaces 30 and 36 to allow air to circulate to the woman's breast B1 to prevent local irritation. The number of air holes 40 is increased from that shown for support 2 in FIGS. 4 and 6 so that even more air can circulate through to the breast B'. Apparatus 32 can be used not only to control lactation, but also to stop lactation. To stop lactation, apparatus 32 must be worn by the lactating woman for extended periods of time until the woman dries up naturally. To make the use of apparatus 32 more comfortable, particularly for women using apparatus 32 to stop lactating, the additional air holes 40 were added. Although ten air holes 40 are shown, the number of air holes 40 can vary as desired.

Figure 10:
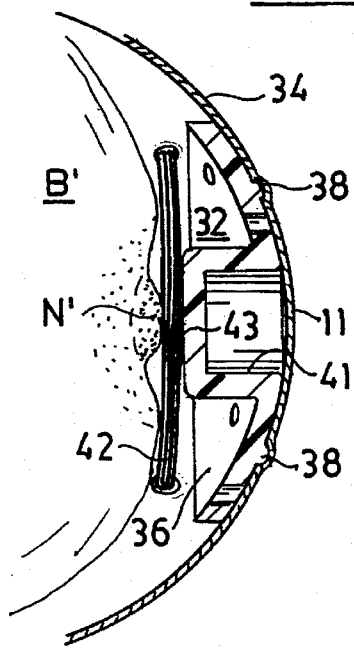
FIG. 10 is a cross-sectional side view of the apparatus taken along line 10—10, including an absorbent breast pad and a brassiere, placed over a human female breast.

Referring to FIG. 10, a cross-sectional view of support 34 taken along line 10—10 in FIG. 9, with an absorbent breast pad 42 and brassiere 11, placed over a human female breast B' are illustrated. Outer surface 30 of support 34 has a convex shape and inner surface 36 of support 34 has a concave surface. Raised ring 38 is located between outer surface 30 and brassiere 11 and through friction helps to hold support 34 in place. A protrusion 41 extends from inner surface 36 out to a nipple contacting surface 43 which in this particular embodiment is substantially flat and operates to depress nipple N' to prevent lactation. Preferably, protrusion 41 is integrated with support 34, although protrusion 41 could be produced separately and then attached to inner surface 36 of support 34. Protrusion 41 has a substantially cylindrical shape with a cross-sectional area which is the same as or larger then the size of a human female nipple, although the shape and size of protrusion 41 can vary as desired. In this particular embodiment, protrusion 41 has a diameter of about ¾". Protrusion 41 can be made from a variety of materials, as long as the material is sufficiently rigid to depress nipple N' when nipple N' is contacted by protrusion 41. Exemplary materials for forming protrusion 41 include any of the rigid plastics known in the art or sufficiently rigidized rubber. The optional absorbent pad 42 is located between nipple contacting surface 43 of projection 41 and nipple N' to absorb any small leakage or excess moisture and to make support 34 more comfortable against breast B'.

Figure 11:
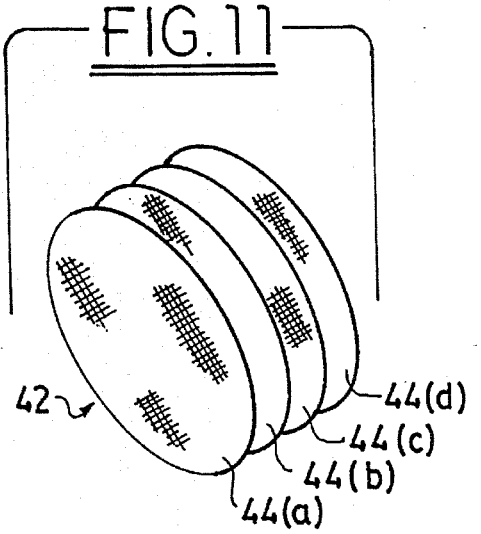
FIG. 11 is an exploded, perspective view of another embodiment for the absorbent breast pad shown in FIG. 10.
Figure 12:
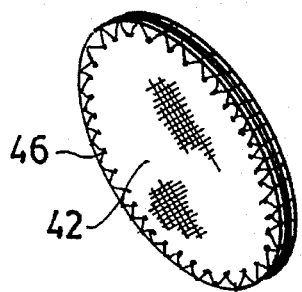
FIG. 12 is a perspective view of the absorbent breast pad shown in FIG. 11.

Referring to FIGS. 11–12, absorbent breast pad 42 is constructed with four layers 44(a–d) of absorbent material which are joined together by stitches 46 along an outside edge of layers 44(a–d). In this particular embodiment, each layer 44(a–d) has a substantially circular shape and is made from cotton, although other shapes and materials could be used. If additional layers were added, then the thickness of the pad 42 would cause protrusion 41 for support 34 to slip out of place. If fewer layers were used, then the pad 42 would provide less comfort to the user.

Unlike apparatus 1, apparatus 32 is designed to be used on a breast B' with an inverted nipple N' as shown in FIG. 10. To use apparatus 32, outer surface 30 of support 34 is placed inside and against the cup of brassiere 11. Although not shown, support 34 may also be integrated with (e.g., sewn into) the cup of brassiere 11. Once apparatus 32 is in place, then brassiere 11 is put on by the woman locating apparatus 32 over breast B' and, in particular, locating substantially flat, nipple-contacting surface 43 against nipple N'. Optional absorbent pad 42 may be placed between breast B' and substantially flat, nipple contacting surface 43 of protrusion 41 before or after brassiere 11 is in place. Raised ring 38 holds support 30 in place against brassiere 11 because of friction. Once apparatus 32 is in place against breast B', brassiere 11 applies sufficient pressure on substantially flat, nipple contacting surface 43 of protrusion 41 to depress nipple N' preventing the release of milk.

When a woman has an inverted nipple, apparatus 32 with substantially flat, nipple contacting surface 43 is preferable over apparatus 1 with concave, nipple contacting surface. If the latter apparatus were used, the outer edges of the concave, nipple contacting surface would dig into the areolar region of the breast. With the substantially flat, nipple contacting surface 43, inverted nipple N' is compressed without undue pressure from the edge of the nipple contacting surface 43 cutting into the areolar region.

Although the invention has been described in detail, for the purpose of illustration, it is understood that such detail is for that purpose and variations can be made therein by those skilled in the art without departing from the spirit and scope of the invention which is defined by the following claims.

What is claimed is:

1. An apparatus for the control of human lactation comprising a support having an outer surface and an inner surface that is shaped to conform substantially to a human female breast, said inner surface having a substantially rigid protrusion with a substantially flat, nipple-contacting surface extending away from said support and positioned to align substantially with and contact a nipple of said human female breast when said apparatus is placed over said human female breast, whereby said protrusion substantially prevents said human female breast from lactating.

2. The apparatus according to claim 1, wherein said outer surface is convex and said inner surface is concave.

3. The apparatus according to claim 1, wherein said protrusion is substantially the same size as said nipple.

4. The apparatus according to claim 1, wherein said protrusion is substantially larger than said nipple.

5. The apparatus according to claim 1, wherein said support is constructed from a flexible material.

6. The apparatus according to claim 5, wherein said flexible material is a plastic.

7. The apparatus according to claim 1 further comprising a brassiere having a cup, wherein said support is placed in side the cup of said brassiere.

8. The apparatus according to claim 7, wherein said brassiere is a conventional brassiere.

9. The apparatus according to claim 7, wherein said brassiere is a nursing brassiere.

10. The apparatus according to claim 1, further comprising an absorbent breast pad placed on said inner surface of said support.

11. The apparatus according to claim 10, wherein said absorbent breast pad comprises four layers.

12. An apparatus for the control of human lactation comprising a flexible support having an outer convex surface and an inner concave surface that is shaped to conform substantially to a human female breast, said inner surface having a substantially flat protrusion extending away from said support and positioned to align substantially with and contact a nipple of said human female breast when said apparatus is placed over said human female breast, whereby said protrusion substantially prevents said human female breast from lactating.

13. The apparatus according to claim 1, wherein said apparatus further comprises a brassiere with which said support is integrated.

14. A method for controlling human lactation comprising the steps of:

providing an apparatus comprising a support having an outer surface and an inner surface that is shaped to conform substantially to a human female breast, said inner surface having a substantially rigid protrusion with a substantially flat, nipple-contacting surface extending away from said support and positioned to align substantially with and contact a nipple of said human female breast when said apparatus is placed over said human female breast, whereby said protrusion substantially prevents said human female breast from lactating;

placing said apparatus over said breast;

positioning said apparatus to align said protrusion substantially with and contact said nipple of said breast; and applying pressure to said apparatus sufficient to prevent said breast from lactating.

15. The method according to claim 14, wherein said outer surface is convex and said inner surface is concave.

16. The method according to claim 14, wherein said protrusion is substantially the same size as said nipple.

17. The method according to claim 14, wherein said protrusion is substantially larger than said nipple.

18. The method according to claim 14, wherein said support is constructed from a flexible material.

19. The method according to claim 18, wherein said flexible material is plastic.

* * * * *